United States Patent
Tokumaru et al.

(10) Patent No.: US 9,677,041 B2
(45) Date of Patent: *Jun. 13, 2017

(54) CULTURE APPARATUS WITH CONDENSATION CONTROL

(71) Applicant: PANASONIC HEALTHCARE HOLDINGS CO., LTD., Tokyo (JP)

(72) Inventors: Tomoyoshi Tokumaru, Ehime (JP); Masahiko Kobayashi, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/860,477

(22) Filed: Sep. 21, 2015

(65) Prior Publication Data

US 2016/0010048 A1 Jan. 14, 2016

Related U.S. Application Data

(63) Continuation of application No. PCT/JP2014/001633, filed on Mar. 20, 2014.

(30) Foreign Application Priority Data

Mar. 22, 2013 (JP) .................................. 2013-059977
Sep. 24, 2013 (JP) .................................. 2013-196429

(51) Int. Cl.
*C12M 1/34* (2006.01)
*C12M 1/00* (2006.01)

(52) U.S. Cl.
CPC ............ *C12M 41/14* (2013.01); *C12M 41/00* (2013.01); *C12M 41/34* (2013.01)

(58) Field of Classification Search
CPC ...... C12M 29/24; C12M 41/00; C12M 41/14; C12M 41/24; C12M 41/34

(Continued)

(56) References Cited

U.S. PATENT DOCUMENTS 5,219,020 A * 6/1993 Akachi .................. F28D 15/02
  165/104.14
5,773,287 A    6/1998 Binder
(Continued)

FOREIGN PATENT DOCUMENTS

EP   2573162 A1   3/2013
JP   5-227942 A   9/1993
(Continued)

OTHER PUBLICATIONS

International Search Report PCT/JP2014/001633 dated Jun. 10, 2014 with English translation.

*Primary Examiner* — Gautam Prakash
(74) *Attorney, Agent, or Firm* — McDermott Will & Emery LLP

(57) ABSTRACT

A culture apparatus is provided which can suppress condensation on walls of a culture space and the like to suppress adverse effects on a culture material. In the culture apparatus having a culture space formed in a heat insulating box main body, a humidification water reservoir for humidifying the culture space and a heat transfer condensation member penetrating the heat insulating box main body are provided. One end of the heat transfer condensation member is disposed inside the culture space, while the other end is disposed outside the heat insulating box main body. The heat transfer condensation member is positioned such that a condensation portion disposed inside the culture space is inclined downward to the one end, and the one end leads condensed water condensed on the surface of the condensation portion into the humidification water reservoir.

16 Claims, 9 Drawing Sheets

(58) Field of Classification Search
USPC .................................................... 435/303.1
See application file for complete search history.

(56) References Cited

U.S. PATENT DOCUMENTS

| | | | |
|---|---|---|---|
| 7,754,477 B2 * | 7/2010 | Osawa ................... | C12M 23/48 219/407 |
| 2004/0188419 A1 * | 9/2004 | Fukuda .................... | H05B 3/34 219/549 |
| 2005/0084420 A1 | 4/2005 | Osawa et al. | |
| 2005/0084956 A1 | 4/2005 | Tamaoki et al. | |
| 2009/0323886 A1 * | 12/2009 | El-genk .............. | F28D 15/0233 376/402 |
| 2012/0198859 A1 * | 8/2012 | Sepulveda .............. | F25B 21/02 62/3.1 |
| 2012/0211201 A1 * | 8/2012 | Kunstwadl ............ | F21V 29/004 165/104.21 |
| 2013/0078714 A1 * | 3/2013 | Yamasaki .............. | C12M 41/14 435/303.1 |
| 2013/0089924 A1 | 4/2013 | Yamasaki et al. | |

FOREIGN PATENT DOCUMENTS

| | | |
|---|---|---|
| JP | 8-242843 A | 9/1996 |
| JP | 2005-95097 A | 4/2005 |
| JP | 2005-118021 A | 5/2005 |
| JP | 2013-66436 A | 4/2013 |

* cited by examiner

US 9,677,041 B2

CULTURE APPARATUS WITH CONDENSATION CONTROL

This application is a Continuation Application of PCT/JP2014/001633 filed Mar. 20, 2014, which claims priority to Japanese Patent Application No. 2013-059977 filed Mar. 22, 2013, and Japanese Patent Application No. 2013-196429 filed Sep. 24, 2013. The subject matter of each is incorporated herein by reference in entirety.

TECHNICAL FIELD

The present invention relates to a culture apparatus that cultures a culture material such as a cell and a microorganism in a culture area.

BACKGROUND ART

There are culture apparatuses that culture culture materials such as cells and microorganisms in incubators. Such a culture apparatus is provided with a heater to heat the inside of the incubator in which a humidification water reservoir is put. For example, the inside of the incubator is kept at a predetermined temperature (for example, 37° C.) and a predetermined humidity (for example, 95% RH) corresponding to the predetermined temperature by controlling the heater.

For example, there is a disclosed culture apparatus that has a bottom heater for heating water in a humidification water reservoir, a heater for heating the inside of an incubator other than the humidification water reservoir, and another heater attached to a heat insulating door hinged on a heat insulating box main body in an openable and closable manner. The three kinds of heaters are independently controlled to keep the temperature of the water in the humidification water reservoir lower than the temperature inside the incubator, so that supersaturated water inside the incubator is returned to the humidification water reservoir, thus suppressing condensation (for example, refer to Patent Literature 1).

This culture apparatus is provided with a temperature sensor to detect the temperature inside the incubator and another temperature sensor to detect an ambient temperature. The three kinds of heaters are independently controlled on the basis of the detection results of the two temperature sensors.

CITATION LIST

Patent Literature

Patent Literature 1: Japanese Patent Application Laid-Open No. Hei. 5-227942

SUMMARY OF INVENTION

Technical Problem

By the way, since heaters work not for cooling but only for heating in general, for example, each of the temperature sensors requires detection accuracy to the certain extent in order to maintain the predetermine relationship between the temperature of the water in the humidification water reservoir and the temperature inside the incubator by the control of the heaters, as described in the above culture apparatus disclosed in Patent Literature 1. The predetermined relationship between the two temperatures herein refers to a relationship in which the temperature of the water in the humidification water reservoir is lower than the temperature inside the incubator to such an extent that the inside of the incubator is maintained at a humidity near the density of saturated water vapor, while suppressing condensation at a place in the incubator at which a culture material is possibly affected. To realize this, however, the temperature of the humidification water reservoir becomes low, so that there is a problem in which condensation occurs around the humidification water reservoir.

The occurrence of the condensation causes a problem in which bacteria occurring in condensed water adversely affect the culture material.

The present disclosure provides a culture apparatus that can suppress condensation to suppress adverse effects on a culture material.

Solution to Problem

A culture apparatus according to this disclosure to solve the above-described problem includes: a heat insulating box main body approximately in a box shape, formed with a culture space therein for culturing a sample such as a cell and a microorganism; a humidification water reservoir disposed in a bottom of the culture space, the humidification water reservoir storing humidification water to control humidity of the culture space; and a heat transfer condensation member penetrating the heat insulating box main body in such a manner that one end is disposed inside the culture space while the other end is disposed outside the heat insulating box main body.

Here, the heat transfer condensation member is positioned such that a condensation portion disposed inside the culture space is inclined downward to the one end, and the one end leads condensed water condensed on a surface of the condensation portion into the humidification water reservoir.

Also, a culture apparatus according to this disclosure includes: a heat insulating box main body approximately in a box shape, formed with a culture space therein for culturing a sample such as a cell and a microorganism; a humidification water reservoir disposed in a bottom of the culture space, the humidification water reservoir storing humidification water to control humidity of the culture space; and a heat transfer condensation member penetrating the heat insulating box main body in such a manner that one end is disposed inside the culture space while the other end is disposed outside the heat insulating box main body.

Here, the heat transfer condensation member is positioned such that one end of a condensation portion disposed inside the culture space leads condensed water condensed on a surface of the condensation portion into the humidification water reservoir. The heat insulating box main body has an approximately box-shaped inner box for forming the culture space and an approximately box-shaped outer box enclosing an outer periphery of the inner box. A first heat insulating sealing member with heat insulating properties and hydrophobic properties is disposed between the inner box and a portion of the heat transfer condensation member that penetrates the inner box. The first heat insulating sealing member has an extending portion that extends into the culture space and that is inclined downward to the one end of the heat transfer condensation member, to lead condensed water adhering to a periphery of the extending portion into the humidification water reservoir.

Advantageous Effects of Invention

The culture apparatus according to this disclosure is designed such that the condensed water condensed on the surface of the condensation portion or the first heat insulating sealing member is led into the humidification water reservoir. Thus, since moisture condensed on the condensation portion or the first heat insulating sealing member is caused to flow downward into the humidification water reservoir to be reusable as the humidification water, it is possible to suppress the occurrence of condensation on walls of the culture space and suppress adverse effects on a culture material.

DESCRIPTION OF EMBODIMENTS

Figure 1:
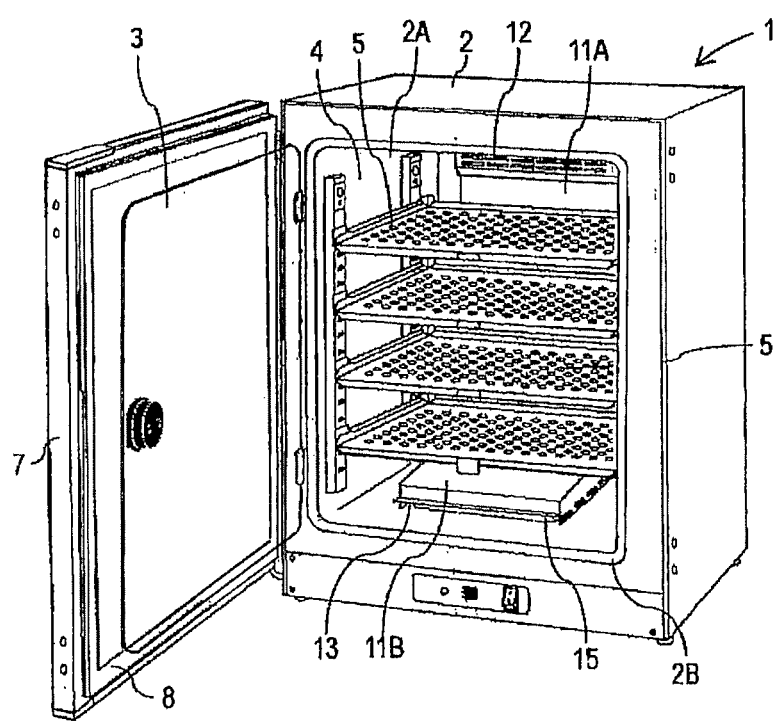
FIG. 1 is a perspective view for explaining a culture apparatus according to an example of this disclosure in a state of opening a heat insulating door.

A culture apparatus 1 according to an example of this disclosure includes: an approximately box-shaped heat insulating box main body formed with an inner box 22 having a culture space 4 therein to culture a sample such as a cell and a microorganism; a humidification water reservoir 15 that retains humidification water for controlling the humidity of the culture space 4 and is disposed in the bottom of the culture space 4; and a heat transfer condensation member 35 penetrating the heat insulating box main body 2 such that one end is disposed inside the culture space 4 while the other end is disposed outside the heat insulating box main body 2. A portion of the heat transfer condensation member 35 that penetrates the inner box 22 and the inner box 22 are disposed with a heat insulating sealing member 36 interposed therebetween. An extending portion of the heat insulating sealing member 36 extending into the culture space 4 is formed with an inclined surface inclined obliquely downward in a forward direction so as to lead condensed water adhering to the periphery of the extending portion into the humidification water reservoir 15. Embodiments of this disclosure will be hereinafter described in detail based on the drawings.

Figure 2:
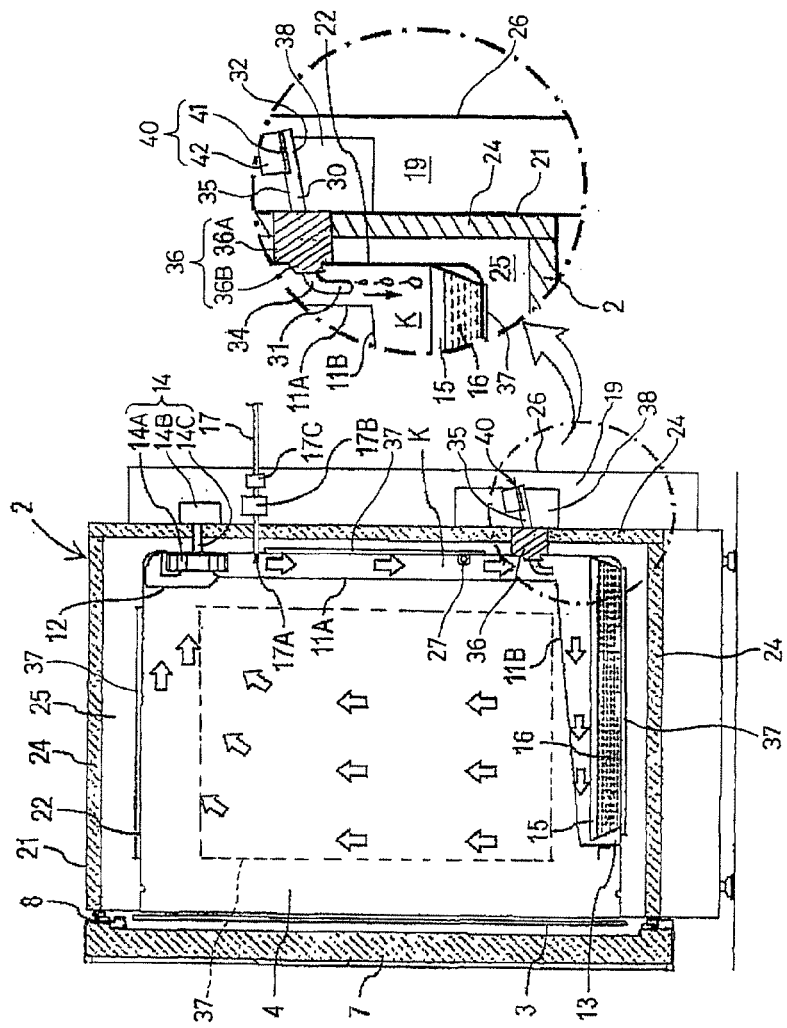
FIG. 2 is a cross-sectional explanatory view in which an incubator is seen from the right side to explain air circulation with focusing on a culture space and a duct in the culture apparatus according to the example of this disclosure.
Figure 3:
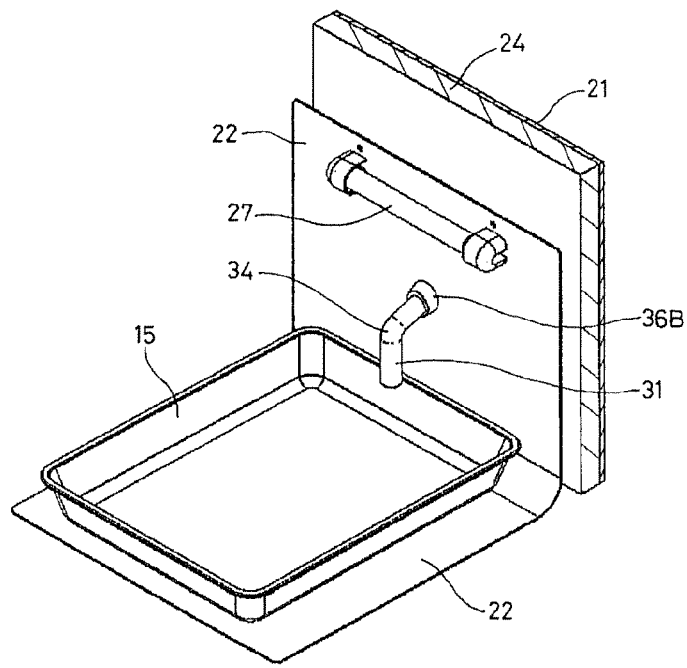
FIG. 3 is a perspective view for explaining the relationship between a heat transfer condensation member and a humidification water reservoir in the culture apparatus according to the example of this disclosure.
Figure 4:
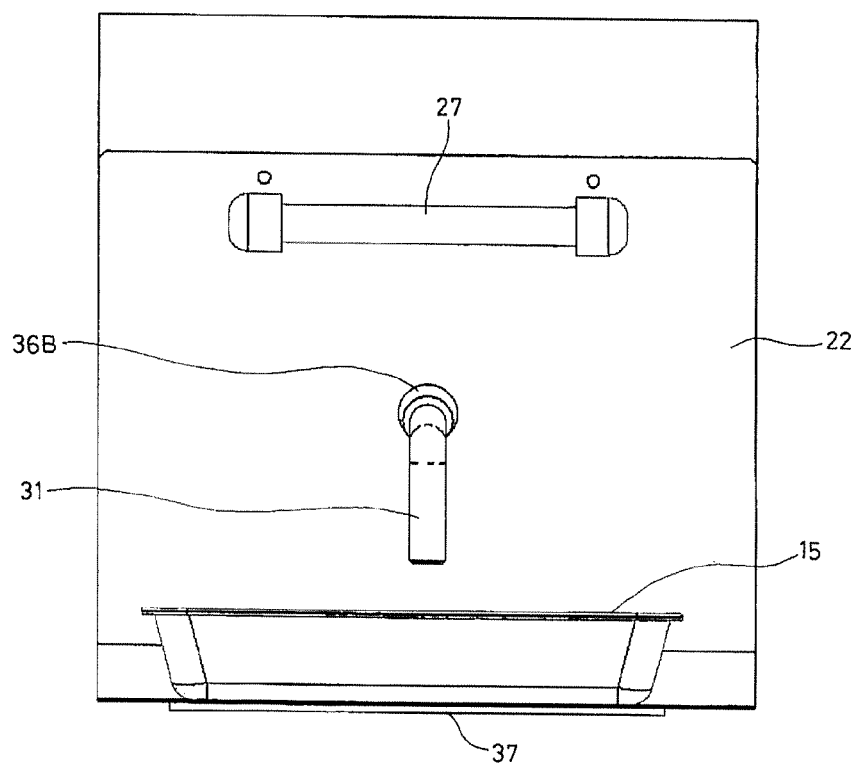
FIG. 4 is a front view for explaining the relationship between the heat transfer condensation member and the humidification water reservoir in the culture apparatus according to the example of this disclosure.

The culture apparatus 1 according to an embodiment of this disclosure will be described with reference to FIGS. 1 to 9. As shown in FIGS. 1 and 2, the culture apparatus 1 according to the embodiment of this disclosure has a left open door (more specifically, an outer door 7 and an inner door 3). The heat insulating box main body 2 having an opening 2A in its front face is approximately in the shape of a box formed with the culture space 4 therein to culture the sample such as a cell and a microorganism. One of the structures, as shown in the drawings, is constituted by a metal outer box 21, a heat insulating material 24 disposed inside the outer box 21, and the front side opened stainless inner box 22 disposed therein with leaving an air layer (so-called air jacket) 25. Thus, the inner box 22 forms the front side opened culture space 4 in the heat insulating box main body 2, serving as an area to culture the sample such as a cell and a microorganism. Heaters 37 are disposed on both left and right side faces, a top face, a bottom face, and a back face of the inner box 22 to heat the culture space 4.

As described above, the culture space 4 for culturing the sample such as a cell and a microorganism is formed in the heat insulating box main body 2 having the opening 2A in its front face. The heat insulating door 7 is attached in an openable and closable manner to one side (left side in the drawing) of the heat insulating box main body 2 as the outer door to keep heat out of the culture space 4 through the front face opening 2A. A loop-shaped gasket 8 with a magnet is disposed in the outer edge of the heat insulating door 7 on a back side. Closing the heat insulating door 7 brings the gasket 8 into tight contact with the outer edge of the front face opening 2A of the heat insulating box main body 2, so that the heat insulating door 7 closes the front face opening 2A in an air-tight manner and keeps outside air out of the culture space 4 through the front face opening 2A.

The culture space 4 is partitioned with the front side opened stainless inner box 22. Both the left and right side faces, the top face, and the back face of the inner box 22 are disposed in the heat insulating box main body 2 with leaving the air layer (so-called air jacket) 25 between each face and the heat insulating box main body 2. A front face opening of the inner box 22 is opened and closed with the transparent door 3 as the inner door. The culture space 4 is substantially formed from a space enclosed with the inner box 22 and the transparent door 3. The transparent door 3 is hinged on the inner box 22 at its left side in an openable and closable manner. An elastic sealing member 2B is disposed in a looped manner at the peripheral edge of the front face opening of the inner box 22. Upon closing the transparent inner door 3, the back side of the transparent inner door 3 comes into tight contact with the elastic sealing member 2B and thus closes the front face opening of the culture space 4.

The culture space 4 is partitioned vertically with a plurality of shelfs 5 (here, into five with four shelfs). If the culture apparatus 1 is, for example, a $CO_2$ incubator, the concentration of $CO_2$ is normally set and kept at the order of 5%, and a $CO_2$ gas is supplied into the culture space 4 after closing the doors to control the concentration of $CO_2$.

In the culture space 4, a duct 11 including a back duct 11A and a bottom duct 11B is disposed with leaving a space with a back wall and a bottom wall of the inner box 22, to form a gas conduit K of air containing $CO_2$ and the like along the back face and the bottom face. To perform forced circulation of air, a gas containing $CO_2$ and the like in the culture space 4 is sucked from a suction port 12 formed at the top of the back duct 11A, and blown into the culture space 4 from outlet ports 13 provided at the front and side faces of the bottom duct 11B. A circulation blower 14 is disposed inside the duct 11 (here, at the top) to perform the forced circulation of the gas containing $CO_2$ and the like. This blower 14 is constituted by a fan 14A, a motor 14B, and a shaft 14C. The motor 14B is disposed in a machine chamber 19 on the outside back face of the heat insulating box main body 2, to be described later. The shaft 14C extends from the motor 14B disposed in the machine chamber 19 through the back face of the heat insulating box main body 2 into the gas conduit K of $CO_2$ and the like and is coupled to the fan 14A.

As the humidification water reservoir 15 for humidifying the culture space 4, the top face opened humidification water reservoir 15 is put in the duct 11 that is on the bottom of the culture space 4 and between the bottom duct 11B and the bottom wall of the inner box 22, to store water for humidification (that is, humidification water) 16. The water is heated and evaporated by the heater 37 disposed on the outside bottom face of the metal, e.g., stainless, inner box 22. It is noted that disposing the humidification water reservoir 15 in the duct 11 and on the bottom of the culture space 4 facilitates circulating humidified gas with high efficiency through the gas conduit K of $CO_2$ and the like, which is formed from the circulation blower 14 and the duct 11.

The machine chamber 19, which contains the motor being drive means for the circulation blower 14, gas supply means 17 for supplying the $CO_2$ gas to the culture space 4, and an electrical component box 38 to accommodate electrical components such as a not-shown control board and the like, is formed of a rear cover 26, for covering the back face of the outer box 21, on the back face of the outer box 21 of the heat insulating box main body 2.

The gas supply means 17 includes a gas supply pipe 17A, an openable valve 17B, a filter 17C, and the like. A tip end portion of the gas supply pipe 17A faces to the gas conduit K.

The $CO_2$ gas supplied from the gas supply pipe 17A can be ejected to control the gas concentration of the culture space 4. To obtain a bactericidal effect on the gas flowing in the culture space 4 and the water 16 in the humidification water reservoir 15, an ultraviolet lamp 27 is disposed in the gas conduit K.

As shown in FIG. 2 and the like, the heat transfer condensation member 35 in which a condensation portion 31 at one end and a cooling portion 32 at the other end are integrated through a connection portion 30 is attached to a predetermined position of the culture apparatus 1. The heat transfer condensation member 35 may be any of a heat pipe in which an operating fluid is sealed, a round bar of a predetermined length made of a heat conductive material such as aluminum, and a flat plate of a predetermined length made of a heat conductive material such as aluminum.

Figure 9:
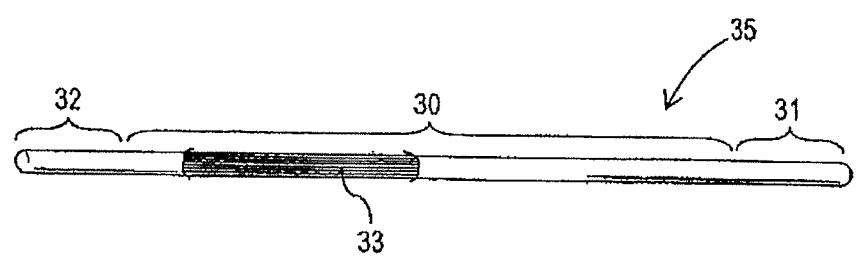
FIG. 9 is an explanatory view for explaining a heat pipe to be used as the heat transfer condensation member in the example of this disclosure.

FIG. 9 shows the structure of a heat pipe 35, which is a kind of heat transfer condensation member 35. The heat pipe 35 has a bar-shaped airtight container in which a little amount of liquid (operating fluid) is vacuum-sealed, and a capillary structure (wicks) 33 in its inner wall. The operating fluid is evaporated at the condensation portion 31 (absorbs latent heat of vaporization), and the evaporated vapor moves to the direction of the cooling portion 32. The vapor is condensed to release the latent heat of vaporization at the cooling portion 32. The condensed fluid is refluxed to the condensation portion 31 by a capillary phenomenon. Such a series of phase changes occurs in a sequential manner, thus accelerating heat transfer.

To accelerate the heat transfer in the heat transfer condensation member 35, the heat pipe 35 is preferably used. However, in a case where extremely short-time heat transfer is not necessarily required, just as with the culture apparatus 1, the heat transfer condensation member 35 may be any of the round bar of a predetermined length made of the metallic heat conductive material such as aluminum and silver and the flat plate of a predetermined length made of the heat conductive material such as aluminum and silver. In the case of aluminum, an antiproliferative effect on germs is obtained by forming an antibacterial coating on the surface of the heat transfer condensation member 35 by antibacterial plating, antibacterial alumite, or the like. It is conceivable to use a copper material for the heat transfer condensation member 35, but the copper is likely to form patina and therefore requires a plating process and the like to prevent the patina from appearing in its surface.

The following embodiments describe the case of adopting the heat transfer condensation member 35 that is made of the round bar of a predetermined length made of the heat conductive material such as aluminum, which is a kind of heat transfer condensation member 35.

The heat transfer condensation member 35 is attached such that the cooling portion 32 is disposed outside the heat insulating box main body 2, that the connection portion 30 is disposed in the culture space 4 in the heat insulating box main body 2 through the heat insulating box main body 2 and the inner box 22, and that the condensation portion 31 is disposed in the gas conduit K in the duct 11A. The cooling portion 32 is disposed in the machine chamber 19 on the back side of the culture apparatus 1 so as not to be damaged by external forces from the vicinity of the culture apparatus 1.

At a portion of the connection portion 30 that penetrates the heat insulating box main body 2 and the inner box 22, the connection portion 30 is disposed at least between the metal outer box 21 and the stainless inner box 22 with the heat insulating sealing member 36 interposed therebetween. The interposition of the heat insulating sealing member 36 prevents the gas flowing through the gas conduit K from leaking and adversely affecting the culture space 4, and prevents the occurrence of condensation on a contact portion between the connection portion 30 and the inner box 22. It is also possible to reduce thermal effects on the outer box 21 and the inner box 22.

To keep the condensation portion 31 at a dew-point temperature and cause condensation on the surface of the condensation portion 31, the cooling portion 32 is cooled to an appropriate temperature. The cooling effect is transmitted to the condensation portion 31 through the connection portion 30, so that the condensation portion 31 is kept at the dew-point temperature. For this reason, an electronic cooling device 40 is attached to the cooling portion 32 to cool the cooling portion 32 to the appropriate temperature. For the sake of achieving ease of attachment, miniaturization, ease of temperature control, and the like, in an example of this disclosure, an electronic cooling element 41 called Peltier element for cooling the cooling portion 32 by the Peltier effect and a heatsink 42 for dissipating heat of the electronic cooling element 41 are provided as the electronic cooling device 40.

In the electronic cooling element 41 called the Peltier element, a plurality of p-n junction semiconductor devices constitute a cooling and heating portion. In a state where n-type semiconductors and p-type semiconductors are arrayed alternately in a lateral direction, a heat absorbing portion (cooling side) is made by coupling an end of the n-type semiconductor to an end of the adjoining p-type semiconductor with a heat conductive plate, and a heat radiating portion (heating side) is made by coupling the other end of the n-type semiconductor to the other end of the adjoining p-type semiconductor with a heat conductive plate. Therefore, on the basis of this relationship, the electronic cooling element 41 has a well-known structure in which the n-type semiconductors and the p-type semiconductors are connected in series as a whole.

The heatsink 42, made of aluminum, has a plate-shaped base 42A and a plurality of plate-shaped radiating fins 42B formed on the top face of the plate-shaped base 42A with leaving space in an integral manner.

Figure 7:
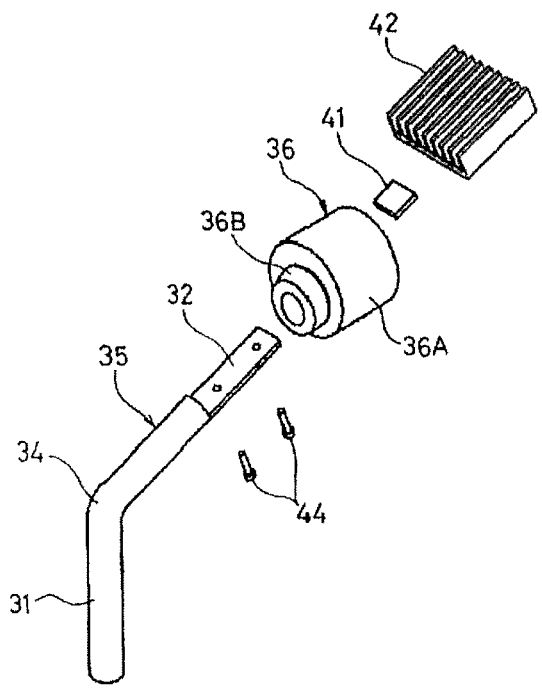
FIG. 7 is an exploded perspective view showing the relationship among the heat transfer condensation member, a heatsink, an electronic cooling element, and a heat insulating member in the culture apparatus according to the example of this disclosure.
Figure 8:
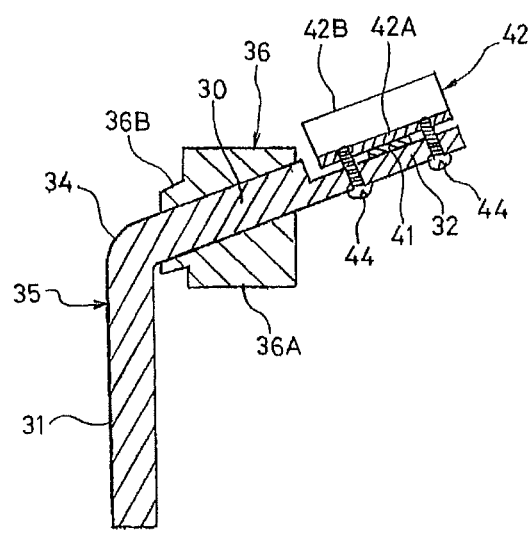
FIG. 8 is a cross-sectional view for explaining the mounting position of the electronic cooling element and the heatsink on the heat transfer condensation member in the culture apparatus according to the example of this disclosure.

As shown in FIGS. 7 and 8, the heat absorbing portion (cooling side) of the electronic cooling element 41 is attached to the top face of the cooling portion 32 of the heat transfer condensation member 35 in a heat conductive state. Thus, the cooling portion 32 of the heat transfer condensation member 35 is formed with a flat attachment surface on its top face. On the attachment surface, the cooling side of the electronic cooling element 41 is disposed with a heat radiating grease or a heat conductive member such as a thin heat conductive rubber sheet interposed therebetween. On the other hand, the plate-shaped base 42A of the heatsink 42, which functions as a radiator, is disposed on the heat radiating portion (heating side) of the electronic cooling element 41 with a heat radiating grease or a heat conductive member such as a thin heat conductive rubber sheet interposed therebetween. In this state, as shown in FIGS. 7 and 8, mounting screws 44 are secured to the plate-shaped base 42A of the heatsink 42 through the cooling portion 32 from below the cooling portion 32 of the heat transfer condensation member 35 for coupling. Thereby, the cooling portion 32 of the heat transfer condensation member 35, the electronic cooling element 41, and the heatsink 42 are integrated into one unit in a heat conductive state.

To keep the condensation portion 31 of the heat transfer condensation member 35 at the dew-point temperature and cause condensation on the surface of the condensation portion 31, the cooling portion 32 is cooled by the electronic cooling element 41. The cooling portion 32 is disposed on the side of the electrical component box 38 in such a position as to be little affected by heat generated by heat generating components in the electrical component box 38.

Figure 5:
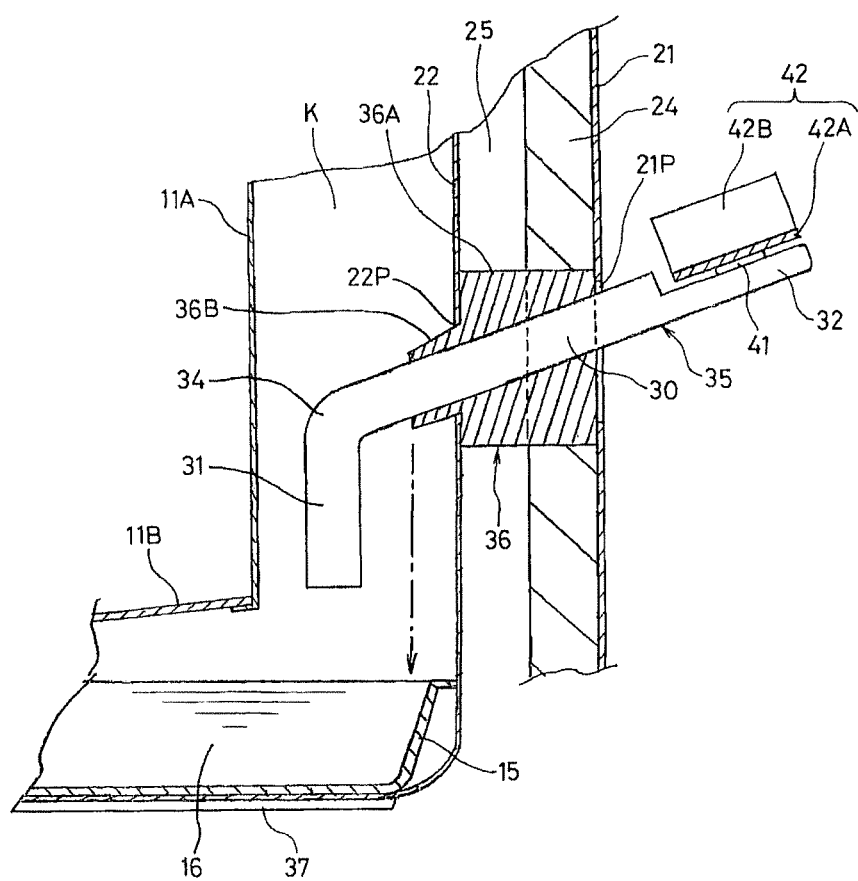
FIG. 5 is a side cross-sectional view for explaining the relationship between the heat transfer condensation member and the humidification water reservoir in the culture apparatus according to the example of this disclosure.
Figure 6:
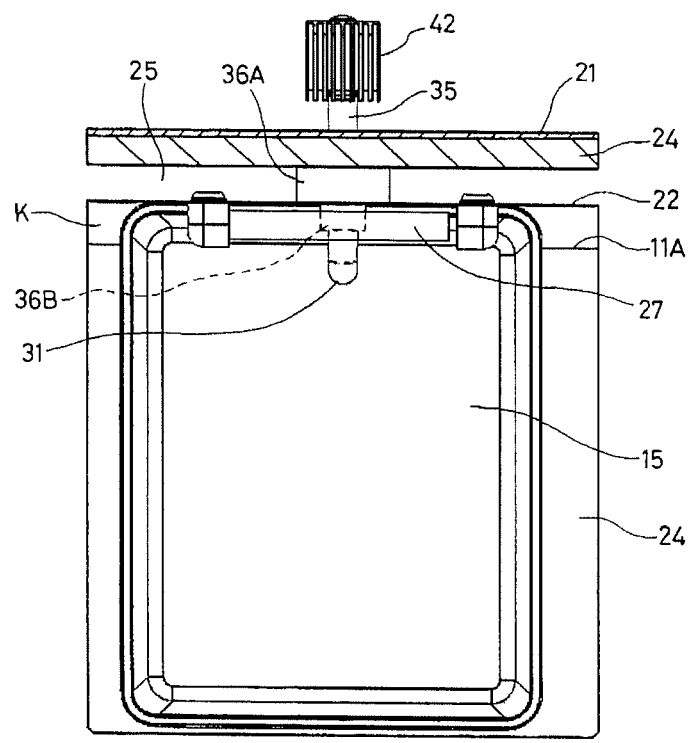
FIG. 6 is a plan view for explaining the relationship between the heat transfer condensation member and the humidification water reservoir in the culture apparatus according to the example of this disclosure.

As shown in FIG. 5, the connection portion 30 of the heat transfer condensation member 35 penetrates a through hole 21P of the outer box 21, the heat insulating sealing member 36, and a through hole 22P of the inner box 22, without being in contact with the outer box 21 and the inner box 22. As shown in the drawings, the heat insulating sealing member 36 is preferably a one-unit member with high hydrophobicity into which a main body portion 36A (second heat insulating sealing member 36A) and a tip sealing portion 36B (first heat insulating sealing member 36B) at a tip thereof are molded, and the heat insulating sealing member 36 is made of a polyacetal resin, by way of example. As a hydrophobic material, there may be adopted a hydrophobic rubber, a fluororesin, or the like. The main body portion 36A of the heat insulating sealing member 36 is in contact with an inner side face of a back wall of the outer box 21 so as to fill the through hole 21P at its back face, and is in contact with a back face of the back wall of the inner box 22 while penetrating the heat insulating material 24. The tip sealing portion 36B extending forward from the main body portion 36A penetrates the through hole 22P of the inner box 22 into the gas conduit K.

As shown in the drawings, the heat transfer condensation member 35 is held in an inclined state such that the connection portion 30 descends from back to front while penetrating the main body portion 36A and the tip sealing portion 36B of the heat insulating sealing member 36. The heat insulating sealing member 36 prevents the gas flowing through the gas conduit K from leaking from the position of the heat transfer condensation member 35, and prevents the adverse effects of the gas leakage on the culture space 4. The heat insulating sealing member 36 also suppresses the occurrence of condensation on the inner box 22 through the connection portion 30 of the heat transfer condensation member 35, and reduces the thermal effects of the outer box 21 and the inner box 22 on the heat transfer condensation member 35.

In order to make moisture that is condensed on the condensation portion 31 and the connection portion 30 in the vicinity thereof flow downward into the humidification water reservoir 15, the heat transfer condensation member 35 is formed with a bend portion 34 by bending downward the connection portion 30 at a portion that reaches the gas conduit K in the duct 11A. A portion of the heat transfer condensation member 35 that extends from the bend portion 34 to the condensation portion 31 is formed downward in parallel with the duct 11A corresponding thereto. Also, in order to make moisture condensed on a portion of the heat insulating sealing member 36 that extends into the duct 11, that is, moisture condensed on the tip sealing portion 36B exposed to the gas conduit K flow downward into the humidification water reservoir 15, the peripheral surface of the tip sealing portion 36B, including not only top and bottom surfaces but also left and right surfaces, takes the form of an inclined surface extending obliquely downward in a forward direction so as to extend directly above the humidification water reservoir 15.

Therefore, condensation tends to occur on the portion of the heat transfer condensation member 35 that extends from the bend portion 34 to the condensation portion 31, and the condensed moisture flows downward by gravity and drops into the humidification water reservoir 15 without dispersal. Even in a case where condensation occurs on the tip sealing portion 36B of the heat insulating sealing member 36 exposed to the gas conduit K, the condensed moisture flows downward along the inclination by gravity and drops into the humidification water reservoir 15 directly or through the connection portion 30 and the condensation portion 31, and therefore drops into the humidification water reservoir 15 without dispersal.

Figure 10:
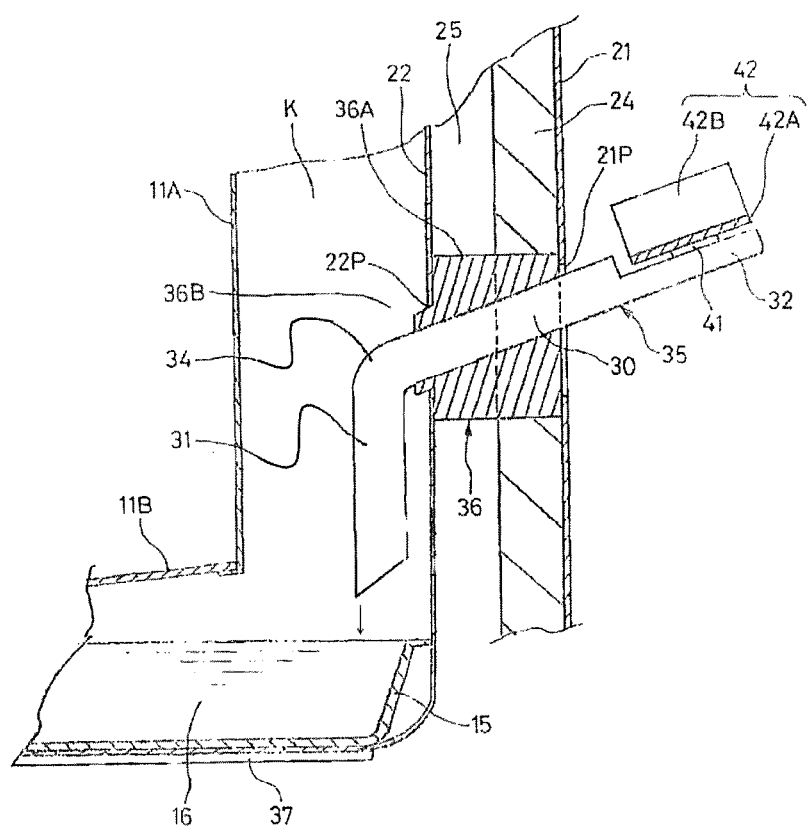
FIG. 10 is a side cross-sectional view for explaining the relationship between the heat transfer condensation member and the humidification water reservoir in another embodiment of the culture apparatus according to the example of this disclosure.

FIG. 10 shows another embodiment. Since components denoted by the same reference numerals as those of FIGS. 1 to 9 have the same functions, the detailed description thereof will be omitted and a different structure will be described. A tip end of the condensation portion 31 is inclined toward the inside of the humidification water reservoir 15, and disposed in such a position that a lowermost end of the condensation portion 31 is situated inside the humidification water reservoir 15 with respect to the edge of the humidification water reservoir 15 in a horizontal direction, in other words, condensed moisture is sure to drop into the humidification water reservoir 15 when flowing downward by gravity. That is to say, the tip end of the condensation portion 31 is inclined so as to be away from the back face of the heat insulating box main body 2. Thereby, even if the condensation portion 31 is brought near to the vicinity of the back face of the heat insulating box main body 2, it is possible to keep a certain distance between the lowermost end of the condensation portion 31 and the back face of the heat insulating box main body 2. It is noted that the heat transfer condensation member 35 penetrates the back face of the heat insulating box main body 2 in the example of this disclosure, but may penetrate a side face thereof.

Figure 11:
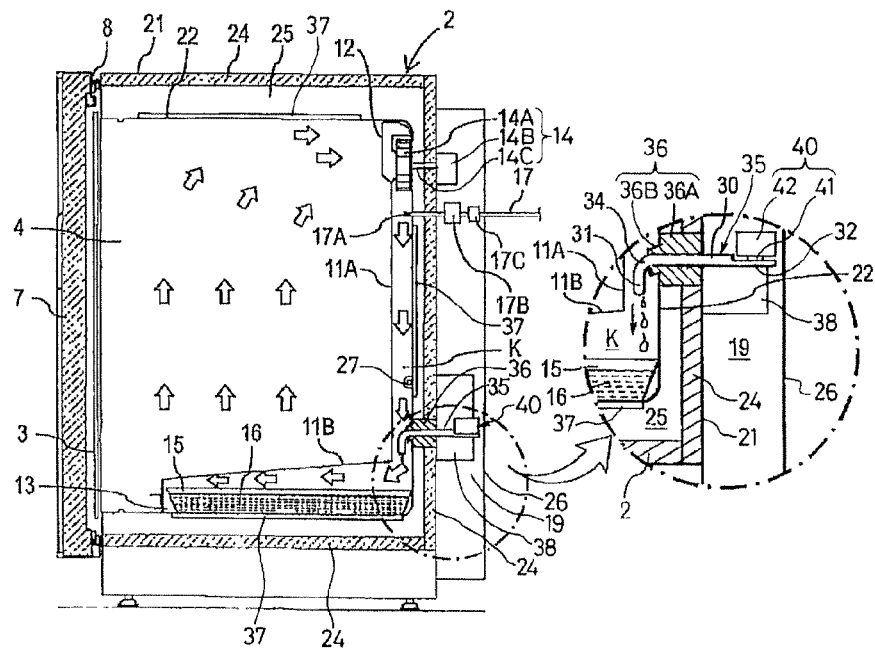
FIG. 11 is a cross-sectional explanatory view in which the incubator is seen from the right side to explain the air circulation with focusing on the culture space and the duct in another embodiment of the culture apparatus according to the example of this disclosure.

FIG. 11 shows yet another embodiment. The heat transfer condensation member 35 shown in FIG. 11 is disposed horizontally, instead of being disposed in an inclined manner with lowering its front side. To be more specific, the heat transfer condensation member 35 is attached so as to dispose the cooling portion 32 outside the heat insulating box main body 2, dispose the connection portion 30 horizontally through the heat insulating box main body 2 and the inner box 22, and dispose the condensation portion 31 in the gas conduit K in the duct 11A. The cooling portion 32 is disposed in the machine chamber 19 of the culture apparatus 1 so as not to be damaged by external forces from the vicinity of the culture apparatus 1.

In a portion of the connection portion 30 that penetrates the inner box 22, the heat insulating sealing member 36 is disposed between the stainless inner box 22 and the connection portion 30. As in the same manner as described above, the heat insulating sealing member 36 is made of a synthetic resin, into which the main body portion 36A and the tip sealing portion 36B at the tip of the main body portion 36A are integrally molded. The main body portion 36A is in contact with the inner side face of the back wall of the outer box 21 at its back face, and is in contact with the back face of the back wall of the inner box 22 through the heat insulating material 24. The tip sealing portion 36B extending forward from the main body portion 36A extends into the gas conduit K through the back wall of the inner box 22. As shown in the drawings, the heat transfer condensation member 35 is held in such a manner that the connection portion 30 thereof is horizontal from back to front while penetrating the main body portion 36A and the tip sealing portion 36B of the heat insulating sealing member 36.

In order to make moisture that is condensed on the condensation portion 31 and the connection portion 30 in the vicinity thereof flow downward into the humidification water reservoir 15, the heat transfer condensation member 35 is formed with the bend portion 34 by bending downward the connection portion 30 at a portion that reaches the gas conduit K in the duct 11A. A portion of the heat transfer condensation member 35 that extends from the bend portion 34 to the condensation portion 31 is formed downward in parallel with the duct 11A corresponding thereto. Also, in order to make moisture condensed on a portion of the heat insulating sealing member 36 that extends into the duct 11, that is, moisture condensed on the tip sealing portion 36B exposed to the gas conduit K flow downward into the humidification water reservoir 15, the peripheral surface of the tip sealing portion 36B, including not only top and bottom surfaces but also left and right surfaces, takes the form of an inclined surface extending obliquely downward in a forward direction so as to extend directly above the humidification water reservoir 15.

Therefore, condensation tends to occur on the portion of the heat transfer condensation member 35 that extends from the bend portion 34 to the condensation portion 31, and the condensed moisture flows downward by gravity and drops into the humidification water reservoir 15 without dispersal. Even in a case where condensation occurs on the tip sealing portion 36B of the heat insulating sealing member 36 exposed to the gas conduit K, the condensed moisture flows downward along the inclination by gravity and drops into the humidification water reservoir 15 directly or through the connection portion 30 and the condensation portion 31, and therefore drops into the humidification water reservoir 15 without dispersal.

As described above, in the example of this disclosure shown in FIGS. 1 to 13, since the heat insulating sealing member 36 is disposed between a portion of the connection portion 30 that penetrates the inner box 22 and the stainless inner box 22, the gas flowing through the gas conduit K does not leak from the position of the heat transfer condensation member 35, thus preventing the adverse effects of the gas leakage on the culture space 4. It is also possible to suppress condensation on the inner box 22 through the connection portion 30 of the heat transfer condensation member 35, and suppress the thermal effects of the outer box 21 and the inner box 22 on the heat transfer condensation member 35.

As in the same manner as described above, the heat absorbing portion (cooling portion) of the electronic cooling element 41 is attached to the cooling portion 32 of the heat transfer condensation member 35 in a heat conductive state. Thus, exerting the same control as described above causes condensation on the surface of the condensation portion 31, and hence the condensed water is led into the humidification water reservoir 15 and reused for humidification.

In the above disclosed technique, in a case where the electronic cooling element 41 promotes heat dissipation from the cooling portion 32 of the heat transfer condensation member 35, making a drive voltage of the electronic cooling element 41 variable on the basis of an ambient temperature of the culture apparatus 1 and the like has the effect of controlling a temperature state so as to cause condensation on the surface of the condensation portion 31. However, the cooling portion 32 of the heat transfer condensation member 35 may be extended and attached in contact with a left side face, a right side face, or a back face of the rear cover 26 for covering the machine chamber 19 through a heat radiating grease or a heat conductive member such as a thin heat conductive rubber sheet, instead of providing the electronic cooling element 41, to thereby dissipate heat of the cooling portion 32 of the heat transfer condensation member 35 through the rear cover 26.

Forming the cooling portion 32 in such a shape as to be in contact with a plurality of surfaces of the outer box 21 and attaching the cooling portion 32 in contact with the outer box 21 through a heat radiating grease or a heat conductive member such as a thin heat conductive rubber sheet make it possible to dissipate heat of the cooling portion 32 through the outer box 21. The heat dissipation from the cooling portion 32 cools the condensation portion 31, and moisture condensed on the surface of the condensation portion 31 is led into the humidification water reservoir 15 disposed beneath.

The size, shape, dimensions, number, and the like of the heat transfer condensation member to be used in this disclosure are variable in accordance with the capacity, shape, and size of the culture apparatus, the culture material, and the like.

It is noted that the above-described embodiments describe the example of this disclosure, but neither limit the invention included in the scope of the claims nor narrow the scope of the claims. The structure of each component in the example of this disclosure is not limited to the above-described embodiments, but variously modified within the technical scope described in the scope of the claims.

As described above, the culture apparatuses 1 according to the embodiments have at least the following effects.

The culture apparatus 1 according to the embodiment includes: the heat insulating box main body 2 approximately in a box shape, formed with the culture space 4 therein for culturing a sample such as a cell and a microorganism; the humidification water reservoir 15 disposed in the bottom of the culture space 4, the humidification water reservoir 15 storing the humidification water to control the humidity of the culture space 4; and the heat transfer condensation member 35 penetrating the heat insulating box main body 2 in such a manner that one end is disposed inside the culture space 4 while the other end is disposed outside the heat insulating box main body 2. The heat transfer condensation member 35 is positioned such that the connection portion 30 (condensation portion) disposed inside the culture space 4 is inclined downward to the one end, and the one end leads condensed water condensed on the surfaces of the connection portion 30 and the condensation portion 31 into the humidification water reservoir 15.

Therefore, since moisture condensed on the connection portion 30 and the condensation portion 31 is caused to flow downward into the humidification water reservoir 15 and is reusable repeatedly as the humidification water 16, it is possible to suppress condensation on the inner walls of the culture space 4 and hence suppress adverse effects on the culture material.

In the culture apparatus 1 according to the embodiment, the heat insulating box main body 2 has the approximately box-shaped inner box 22 for forming the culture space 4 and the approximately box-shaped outer box 21 enclosing the outer periphery of the inner box 22, and the heat insulating sealing member 36 (first heat insulating sealing member) with heat insulating properties and hydrophobic properties is disposed between the inner box 22 and a portion of the heat transfer condensation member 35 that penetrates a side face of the inner box 22.

Thus, due to the hydrophobic properties of the heat insulating sealing member 36, condensed water condensed on the heat insulating sealing member 36 can be caused to promptly flow downward. Furthermore, due to the heat insulating properties of the heat insulating sealing member 36, it is possible to suppress condensation on the inner box 22 through the heat transfer condensation member 35, and suppress thermal effects of the inner box 22 on the heat transfer condensation member 35.

In the culture apparatus 1 according to the embodiment, the tip sealing portion 36B (extending portion) of the heat insulating sealing member 36 that extends into the culture space 4 is inclined downward to the one end of the heat transfer condensation member 35, to lead condensed water adhering to the periphery of the tip sealing portion 36B into the humidification water reservoir 15.

Thus, since condensation on the tip sealing portion 36B of the heat insulating sealing member 36 that extends into the culture space 4 can be promptly led into the humidification water reservoir 15 without dispersal, it is possible to suppress condensation on the walls of the culture space 4 and hence suppress adverse effects on the culture material, and furthermore repeatedly reuse water led into the humidification water reservoir 15 as the humidification water.

The culture apparatus 1 according to the embodiment includes: the heat insulating box main body 2 approximately in a box shape, formed with the culture space 4 therein for culturing a sample such as a cell and a microorganism; the humidification water reservoir 15 disposed in the bottom of the culture space 4, the humidification water reservoir 15 storing the humidification water to control the humidity of the culture space 4; and the heat transfer condensation member 35 penetrating the side face of the heat insulating box main body 2 in such a manner that one end is disposed inside the culture space 4 while the other end is disposed outside the heat insulating box main body 2. The heat transfer condensation member 35 is positioned such that an end of the condensation portion 31 disposed inside the culture space leads condensed water condensed on the surface of the condensation portion 31 into the humidification water reservoir 15. The heat insulating box main body 2 has the approximately box-shaped inner box 22 for forming the culture space 4 and the approximately box-shaped outer box 21 enclosing the outer periphery of the inner box 22. The heat insulating sealing member 36 with heat insulating properties and hydrophobic properties is disposed between the inner box 22 and a portion of the heat transfer condensation member 35 that penetrates the inner box 22. In the heat insulating sealing member 36, the tip sealing portion 36B (extending portion) extending into the culture space 4 is inclined downward to the one end of the heat transfer condensation member 35, to lead condensed water adhering to the periphery of the tip sealing portion 36B into the humidification water reservoir 15.

Therefore, even if the connection portion 30 of the heat transfer condensation member 35 is not inclined, as shown in the embodiment of FIG. 10, since the tip sealing portion 36B is inclined downward in the forward direction, condensed water condensed on the heat insulating sealing member 36 promptly flows downward. Furthermore, due to the heat insulating properties of the heat insulating sealing member 36, it is possible to suppress condensation on the inner box 22 through the heat transfer condensation member 35, and suppress thermal effects of the inner box 22 on the heat transfer condensation member 35. In a case where the connection portion 30 is horizontal, the tip sealing portion 36B preferably covers almost all of the horizontal connection portion 30 in the culture space 4 and extends to the bend portion 34 or the condensation portion 31. This facilitates the prompt flow of the condensed water.

In the culture apparatus 1 according to the embodiment, the second heat insulating sealing member 36A with heat insulating properties covers a portion of the heat transfer condensation member 35 that is disposed between the outer box 21 and the inner box 22.

Therefore, the portion of the heat transfer condensation member 35 that is disposed between the outer box 21 and the inner box 22 is hardly affected by the temperature of the inner box 22 and the outer box 21, and hence has a sufficient condensation effect on the portion extending into the culture space 4.

In the culture apparatus 1 according to the embodiment, the first heat insulating sealing member 36B and the second heat insulating sealing member 36A are integrated into one unit.

Thus, it is possible to facilitate formation and attachment processes of the heat insulating sealing member, which effectively suppresses the temperature effect of surroundings on the heat transfer condensation member 35 and promotes a flow of condensed water downward to the extending portion extending into the culture space 4, thus resulting in cost reduction.

In the culture apparatus 1 according to the embodiment, the heat transfer condensation member 35 is provided with an electronic cooling element 41 that can cool the heat transfer condensation member 35 by the Peltier effect at a cooling portion 32 disposed outside the heat insulating box main body 2, and moisture condensed on the surface of the condensation portion 31 by cooling by the electronic cooling element 41 is led into the humidification water reservoir 15 disposed beneath.

Therefore, it is possible to have control over the temperature so as to cause condensation on the surface of the condensation portion 31, by varying the drive voltage of the electronic cooling element 41.

In the culture apparatus 1 according to another embodiment, the tip end of the condensation portion 31 is inclined toward the inside of the humidification water reservoir 15. In other words, the tip end of the condensation portion 31 is inclined so as to be away from the back face of the heat insulating box main body 2.

Thereby, even if the condensation portion 31 is brought near to the vicinity of the back face of the heat insulating box main body 2, condensed water is reliably caused to flow downward into the humidification water reservoir 15.

Figure 12:
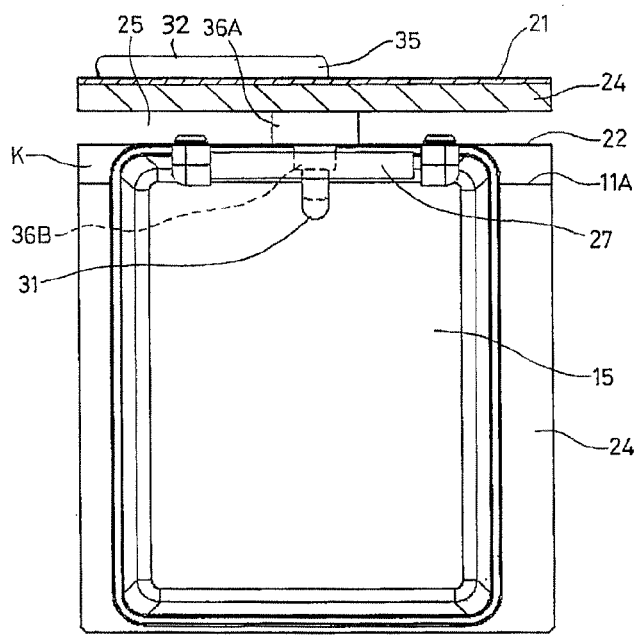
FIG. 12 is a plan view for explaining the relationship in which a cooling portion of the heat transfer condensation member is disposed on an outer box of a heat insulating box main body in a heat conductive state in another embodiment of the culture apparatus according to the example of this disclosure.

In the culture apparatus 1 according to another of the embodiments, as shown in FIG. 12, contact of the cooling portion 32 disposed outside the heat insulating box main body 2 with the outer box 21 facilitates heat dissipation of the heat transfer condensation member 35, and the heat dissipation from the cooling portion 32 cools the condensation portion 31, so that moisture condensed on the surface of the condensation portion 31 is led into the humidification water reservoir 15 disposed beneath.

Thus, utilizing the outer box 21 for the heat dissipation of the cooling portion 32 eliminates the need for providing the electronic cooling element 41, thus resulting in cost reduction.

The cooling portion 32 preferably is caused to be in contact with the outer box 21 through the heat radiating grease or the heat conductive member such as the thin heat conductive rubber sheet.

Thus, heat is effectively dissipated from the cooling portion 32 through the outer box 21.

Figure 13:
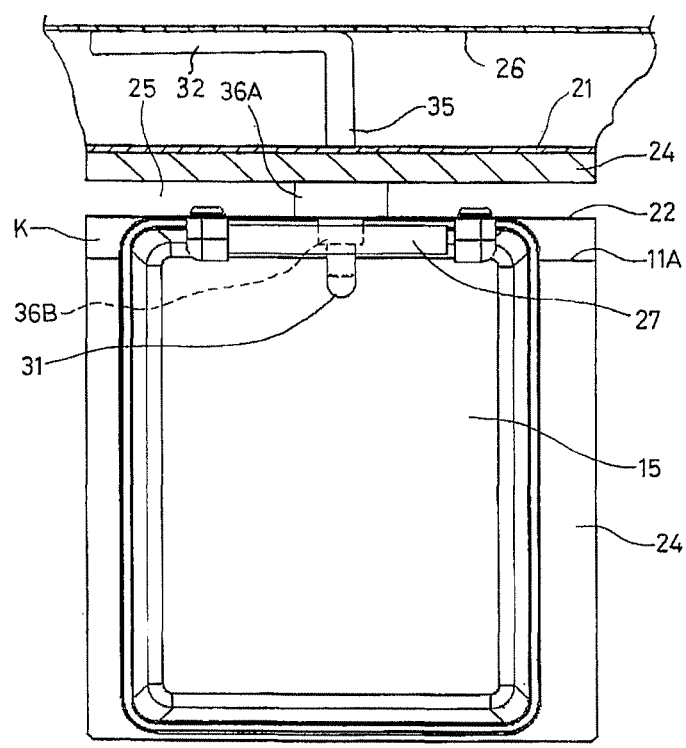
FIG. 13 is a plan view for explaining the relationship in which the cooling portion of the heat transfer condensation member is disposed on a cover member for covering the cooling portion in a heat conductive state in another embodiment of the culture apparatus according to the example of this disclosure.

In the culture apparatus 1 according to another embodiment, at least a cover member 26 for covering the cooling portion 32 of the heat transfer condensation member 35 is provided outside the heat insulating box main body 2. As shown in FIG. 13, heat is dissipated from the cooling portion 32 by the contact with the cover member 26. The heat dissipation from the cooling portion 32 cools the condensation portion 31, and thus moisture condensed on the surface of the condensation portion 31 is led into the humidification water reservoir 15 disposed beneath.

Therefore, the cover member 26 protects the cooling portion 32 from damage by external forces from the vicinity of the culture apparatus 1. Also, utilizing the cover member 26 for the heat dissipation of the cooling portion 32 eliminates the need for providing the electronic cooling element 41, thus resulting in cost reduction.

The cooling portion is preferably caused to be in contact with the cover member 26 through the heat radiating grease or the heat conductive member such as the thin heat conductive rubber sheet.

Thus, heat is effectively dissipated from the cooling portion 32 through the cover member 26.

INDUSTRIAL APPLICABILITY

The culture apparatus according to the example of this disclosure is configured such that the heat transfer condensation member having the condensation portion and the cooling portion is attached to a predetermined position, and for example, the inside vapor density of the culture space closing to the density of over-saturated water vapor causes condensation on the condensation portion, and the condensed moisture flows downward into the humidification water reservoir so as to be repeatedly usable as the humidification water. Therefore, the culture apparatus has the significant effects of suppressing adverse effects on a culture material by suppressing the condensation, allowing operation of the culture space without the occurrence of temperature and humidity variations by operating the circular blower in the duct, and providing the economical culture apparatus without increased manufacturing costs, thus having a great deal of potential in industry.

REFERENCE SIGNS LIST 1 culture apparatus
2 heat insulating box main body
2A opening
3 transparent inner door
4 culture space
5 shelf
7 heat insulating door
8 gasket
11 duct
11A back duct
11B bottom duct
14 circulation blower
15 humidification water reservoir
16 humidification water
17 gas supply means
17A gas supply pipe
21 outer box
22 inner box
24 heat insulating material
25 air layer (air jacket)
30 connection portion
31 condensation portion
32 cooling portion
33 capillary structure (wicks)
34 bend portion
35 heat transfer condensation member
36 heat insulating sealing member
36A main body portion of heat insulating sealing member (second heat insulating sealing member)

36B tip sealing portion of heat insulating sealing member (first heat insulating sealing member)
40 electronic cooling device
41 electronic cooling element
42 heatsink

The invention claimed is:

1. A culture apparatus comprising:
a heat insulating box main body having a box shape and a culture space therein for culturing a sample;
a humidification water reservoir disposed at a bottom of the culture space, the humidification water reservoir for storing humidification water to control humidity of the culture space;
a heat transfer condensation member penetrating the heat insulating box main body and having one end disposed inside the culture space and the other end disposed outside the heat insulating box main body, the heat transfer condensation member includes a condensation portion disposed inside the culture space, the condensation portion is inclined downward toward the humidification water reservoir, the one end leads condensed water condensed on a surface of the condensation portion into the humidification water reservoir; and
a first heat insulating sealing member disposed between the heat insulating box main body and a portion of the heat transfer condensation member that penetrates the heat insulating box main body, the first heat insulating member includes an extending portion that extends along a part of the condensation portion into the culture space, the extending portion is inclined downward toward the humidification water reservoir and leads condensed water adhering to a periphery of the extending portion into the humidification water reservoir.

2. The culture apparatus according to claim 1, wherein the heat insulating box main body has a box-shaped inner box for forming the culture space and a box-shaped outer box enclosing an outer periphery of the inner box, and the first heat insulating sealing member with heat insulating properties and hydrophobic properties is disposed between the inner box and the portion of the heat transfer condensation member that penetrates the inner box.

3. The culture apparatus according to claim 2, further comprising a second heat insulating sealing member with heat insulating properties that covers a portion of the heat transfer condensation member that is disposed between the outer box and the inner box.

4. The culture apparatus according to claim 3, wherein the first heat insulating sealing member and the second heat insulating sealing member are integrated into one unit.

5. The culture apparatus according to claim 1, wherein a tip of the one end is inclined toward the inside of the humidification water reservoir, and a lowermost end of the tip is disposed inside the humidification water reservoir in a horizontal direction with respect to an edge of the humidification water reservoir.

6. The culture apparatus according to claim 1, wherein the heat transfer condensation member includes an electronic cooling element that can cool the heat transfer condensation member by the Peltier effect at a cooling portion of the heat transfer condensation member disposed outside the heat insulating box main body, and moisture condensed on the surface of the condensation portion by cooling by the electronic cooling element is led into the humidification water reservoir disposed beneath.

7. The culture apparatus according to claim 6, wherein heat is dissipated from the heat transfer condensation member by contact of the cooling portion disposed outside the heat insulating box main body with an outer box, and the moisture condensed on the surface of the condensation portion by cooling the condensation portion by heat dissipation from the cooling portion is led into the humidification water reservoir disposed beneath.

8. The culture apparatus according to claim 1, wherein a cover member for covering at least a cooling portion of the heat transfer condensation member is provided outside the heat insulating box main body, heat is dissipated from the cooling portion by contact with the cover member, and moisture condensed on the surface of the condensation portion by cooling the condensation portion by heat dissipation from the cooling portion is led into the humidification water reservoir disposed beneath.

9. A culture apparatus comprising:
a heat insulating box main body having a box shape and a culture space therein for culturing a sample, the heat insulating box main body has a box-shaped inner box for forming the culture space and a box-shaped outer box enclosing an outer periphery of the inner box;
a humidification water reservoir disposed at a bottom of the culture space, the humidification water reservoir for storing humidification water to control humidity of the culture space;
a heat transfer condensation member penetrating the heat insulating box main body and having one end disposed inside the culture space and the other end disposed outside the heat insulating box main body, wherein
the heat transfer condensation member is positioned such that one end of a condensation portion of the heat transfer condensation member disposed inside the culture space leads condensed water condensed on a surface of the condensation portion into the humidification water reservoir; and
a first heat insulating sealing member with heat insulating properties and hydrophobic properties disposed between the inner box and a portion of the heat transfer condensation member that penetrates the inner box, wherein
the first heat insulating sealing member has an extending portion that extends into the culture space and that is inclined downward to the one end of the heat transfer condensation member, to lead condensed water adhering to a periphery of the extending portion into the humidification water reservoir.

10. The culture apparatus according to claim 9, wherein the heat transfer condensation member is positioned such that the condensation portion disposed inside the culture space is inclined downward to the one end of the heat transfer condensation member, and the one end of the heat transfer condensation member leads condensed water condensed on a surface of the condensation portion into the humidification water reservoir.

11. The culture apparatus according to claim 9, wherein a tip of the one end is inclined toward the inside of the humidification water reservoir, and a lowermost end of the tip is disposed inside the humidification water reservoir in a horizontal direction with respect to an edge of the humidification water reservoir.

12. The culture apparatus according to claim 9, further comprising a second heat insulating sealing member with heat insulating properties covers a portion of the heat transfer condensation member that is disposed between the outer box and the inner box.

13. The culture apparatus according to claim 12, wherein the first heat insulating sealing member and the second heat insulating sealing member are integrated into one unit.

14. The culture apparatus according to claim 9, wherein the heat transfer condensation member includes an electronic cooling element that can cool the heat transfer condensation member by the Peltier effect at a cooling portion disposed outside the heat insulating box main body, and moisture condensed on the surface of the condensation portion by cooling by the electronic cooling element is led into the humidification water reservoir disposed beneath.

15. The culture apparatus according to claim 14, wherein heat is dissipated from the heat transfer condensation member by contact of the cooling portion disposed outside the heat insulating box main body with the outer box, and the moisture condensed on the surface of the condensation portion by cooling the condensation portion by heat dissipation from the cooling portion is led into the humidification water reservoir disposed beneath.

16. The culture apparatus according to claim 9, wherein a cover member for covering at least a cooling portion of the heat transfer condensation member is provided outside the heat insulating box main body, heat is dissipated from the cooling portion by contact with the cover member, and moisture condensed on the surface of the condensation portion by cooling the condensation portion by heat dissipation from the cooling portion is led into the humidification water reservoir disposed beneath.

* * * * *